(12) United States Patent
Liu

(10) Patent No.: US 11,253,662 B2
(45) Date of Patent: Feb. 22, 2022

(54) ELECTRONIC CIGARETTE

(71) Applicant: Tuanfang Liu, Shenzhen (CN)

(72) Inventor: Tuanfang Liu, Shenzhen (CN)

(*) Notice: Subject to any disclaimer, the term of this patent is extended or adjusted under 35 U.S.C. 154(b) by 482 days.

(21) Appl. No.: 16/408,427

(22) Filed: May 9, 2019

(65) Prior Publication Data

US 2020/0196677 A1 Jun. 25, 2020

(30) Foreign Application Priority Data

Dec. 20, 2018 (CN) .......................... 201811564134.0
Dec. 20, 2018 (CN) .......................... 201822146642.9

(51) Int. Cl.
| | |
|---|---|
| *A61M 15/06* | (2006.01) |
| *A61M 15/00* | (2006.01) |
| *A24F 40/10* | (2020.01) |
| *A24F 40/40* | (2020.01) |
| *A61M 11/04* | (2006.01) |

(52) U.S. Cl.
CPC ............ *A61M 15/06* (2013.01); *A24F 40/10* (2020.01); *A24F 40/40* (2020.01); *A61M 15/0021* (2014.02); *A61M 11/042* (2014.02); *A61M 2205/8206* (2013.01)

(58) Field of Classification Search
CPC .......................... A61M 15/06; A61M 15/0021; A61M 11/042; A24F 40/00; A24F 40/10; A24F 40/40

See application file for complete search history.

(56) References Cited

U.S. PATENT DOCUMENTS

| | | | |
|---|---|---|---|
| 2015/0305403 A1* | 10/2015 | Coelho Belo Fernandes De Carvalho .............. | A24F 40/485 131/328 |
| 2016/0000145 A1* | 1/2016 | Liu ......................... | A24F 40/60 131/329 |
| 2017/0354182 A1* | 12/2017 | Liu ......................... | A24F 40/40 |
| 2018/0027874 A1* | 2/2018 | Zhu ......................... | F22B 1/284 |
| 2019/0351155 A1* | 11/2019 | Montagnino ......... | A61F 7/0085 |
| 2020/0015524 A1* | 1/2020 | Rado ..................... | H05B 1/0244 |
| 2020/0178612 A1* | 6/2020 | Zhu ......................... | A24F 40/485 |

\* cited by examiner

*Primary Examiner* — Alex B Efta

(74) *Attorney, Agent, or Firm* — Matthias Scholl P.C.; Matthias Scholl

(57) ABSTRACT

An electronic cigarette, including an atomization assembly and a battery assembly. The atomization assembly includes a mouthpiece, a first sealing ring sealing the mouthpiece, an insulating gasket, a first fixing ring fixing the insulating gasket, a mouthpiece holder, a second sealing ring sealing the mouthpiece holder, an observation tube, a cover, an e-liquid chamber, O-rings, a seal plug, a piece of cotton, a heating wire, a limit cover, an insulation ring, and a joint. The atomization assembly includes a mouthpiece, a first sealing ring sealing the mouthpiece, an insulating gasket, a first fixing ring fixing the insulating gasket, a mouthpiece holder, a second sealing ring sealing the mouthpiece holder, an observation tube, a cover, an e-liquid chamber, O-rings, a seal plug, a piece of cotton, a heating wire, a limit cover, an insulation ring, and a joint.

2 Claims, 5 Drawing Sheets

ELECTRONIC CIGARETTE

CROSS-REFERENCE TO RELAYED APPLICATIONS

Pursuant to 35 U.S.C.§ 119 and the Paris Convention Treaty, this application claims foreign priority to Chinese Patent Application No. 201811564134.0 filed Dec. 20, 2018, and to Chinese Patent Application No. 201822146642.9 filed Dec. 20, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

This disclosure relates to an electronic cigarette.

Electronic cigarettes atomize nicotine-containing e-liquid. In conventional electronic cigarettes, the atomization assembly is fixedly connected to the battery assembly, and the e-liquid inlet is immersed in the e-liquid regardless of whether the electronic cigarette is in use (switched on and puffed).

SUMMARY

Provided is an electronic cigarette comprising an atomization assembly and a battery assembly. The atomization assembly is disposed on the battery assembly.

The atomization assembly comprises a mouthpiece, a first sealing ring sealing the mouthpiece, an insulating gasket, a first fixing ring fixing the insulating gasket, a mouthpiece holder, a second sealing ring sealing the mouthpiece holder, an observation tube, a cover, an e-liquid chamber, O-rings, a seal plug, a piece of cotton, a heating wire, a limit cover, an insulation ring, and a joint.

The battery assembly comprises an electrode pole, a third sealing ring sealing the electrode pole, an electrode output, a threaded sealing ring, a second fixing ring, a threaded ring, a fourth sealing ring sealing the threaded ring, a nylon insulation ring, a press button, a control plate, a support, a silica pad, an observation window, a battery core, ring washers, a cartridge, and a battery cover.

The mouthpiece holder comprises a groove and the second sealing ring is embedded in the groove; the insulating gasket is disposed on the mouthpiece holder; the first fixing ring is sheathed on the insulating gasket; the first sealing ring is sheathed on the mouthpiece; the mouthpiece is in threaded connection to the first fixing ring; the cover is disposed on the e-liquid chamber; the cotton is sheathed on the heating wire; the heating wire is disposed in the limit cover; the insulation ring is disposed in the limit cover to separate positive and negative pins of the heating wire; the insulation ring is sheathed on the joint; the O-rings are sheathed on the limit cover; the O-rings, the seal plug, the cotton, the heating wire, the limit cover, the insulation ring, and the joint form an atomization core; the atomization core is disposed in the e-liquid chamber; the seal plug is disposed on one end of the chamber away from the cover; the chamber is in threaded connection to the mouthpiece holder; and the chamber and the mouthpiece holder are disposed in the observation tube.

The third sealing ring, the electrode output, the threaded sealing ring, and the second fixing ring are sheathed on the electrode pole in that order; the electrode pole is disposed in the threaded ring; the nylon insulation ring is sheathed on the electrode pole; the fourth sealing ring is sheathed on the threaded ring; the silica pad is disposed on the control plate; the control plate is disposed on the support; the observation window is fixed on the control plate; the press button is disposed on the support; the support is disposed in the cartridge; the ring washers are disposed on two ends of the battery core, respectively; the ring washers and the battery core are disposed in the cartridge; the battery cover is embedded in a first end of the cartridge away from the mouthpiece; the threaded ring is in threaded connection to a second end of the cartridge opposite to the first end.

When the atomization assembly is not combined with the battery assembly, the e-liquid inlet of the limit cover is separated from the chamber. No e-liquid enters the atomization core. When the atomization assembly is combined with the battery assembly, the electrode pole pushes the atomization core to move towards the chamber, so that the e-liquid inlet of the limit cover enters the chamber, and the e-liquid permeates into the atomization core.

The observation tube comprises female threads, and the threaded ring comprises male threads matching the female threads. The atomization assembly is connected to the battery assembly via the female threads and the male threads. The electronic cigarette is cylindrical. The mouthpiece holder is in threaded connection to the chamber. When the atomization core requires renewal, loosen the threads to detach the mouthpiece holder from the chamber, and the atomization core can be renewed.

DETAILED DESCRIPTION

To further illustrate, embodiments detailing an electronic cigarette are described below. It should be noted that the following embodiments are intended to describe and not to limit the disclosure.

Figure 1:
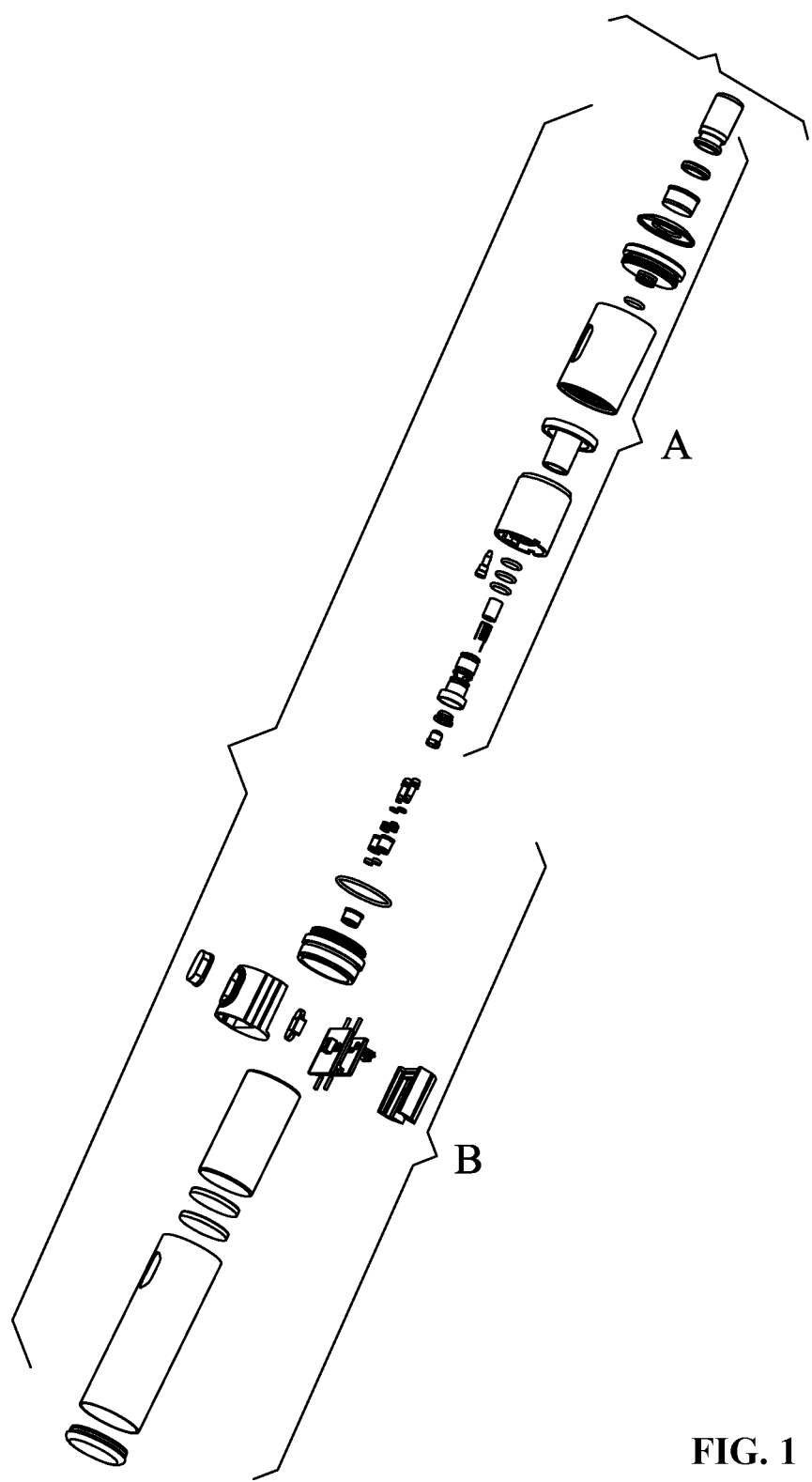
FIG. 1 is an exploded view of an electronic cigarette as described in the disclosure.
Figure 2:
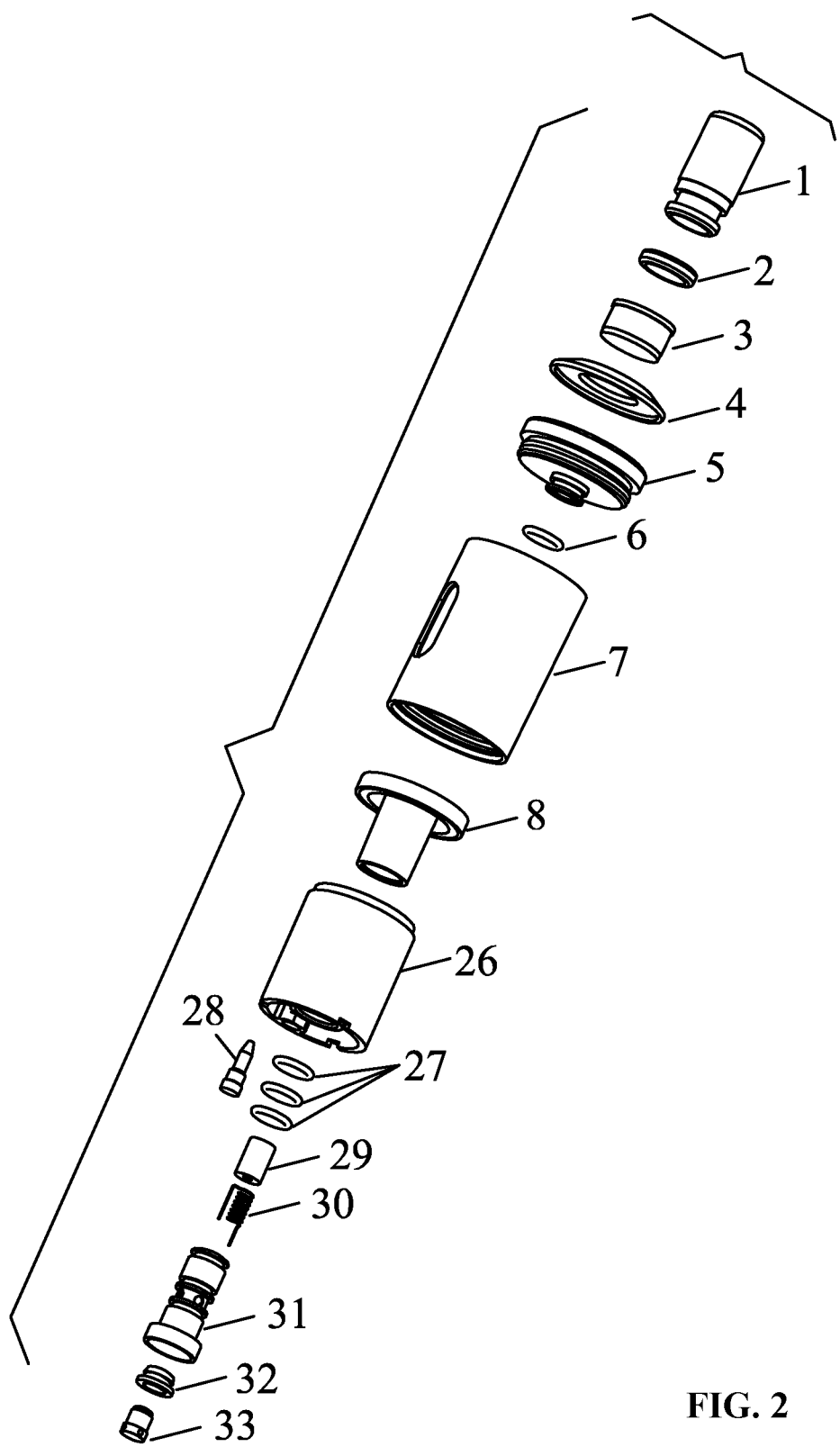
FIG. 2 is an exploded view of an atomization assembly of an electronic cigarette as described in the disclosure.
Figure 3:
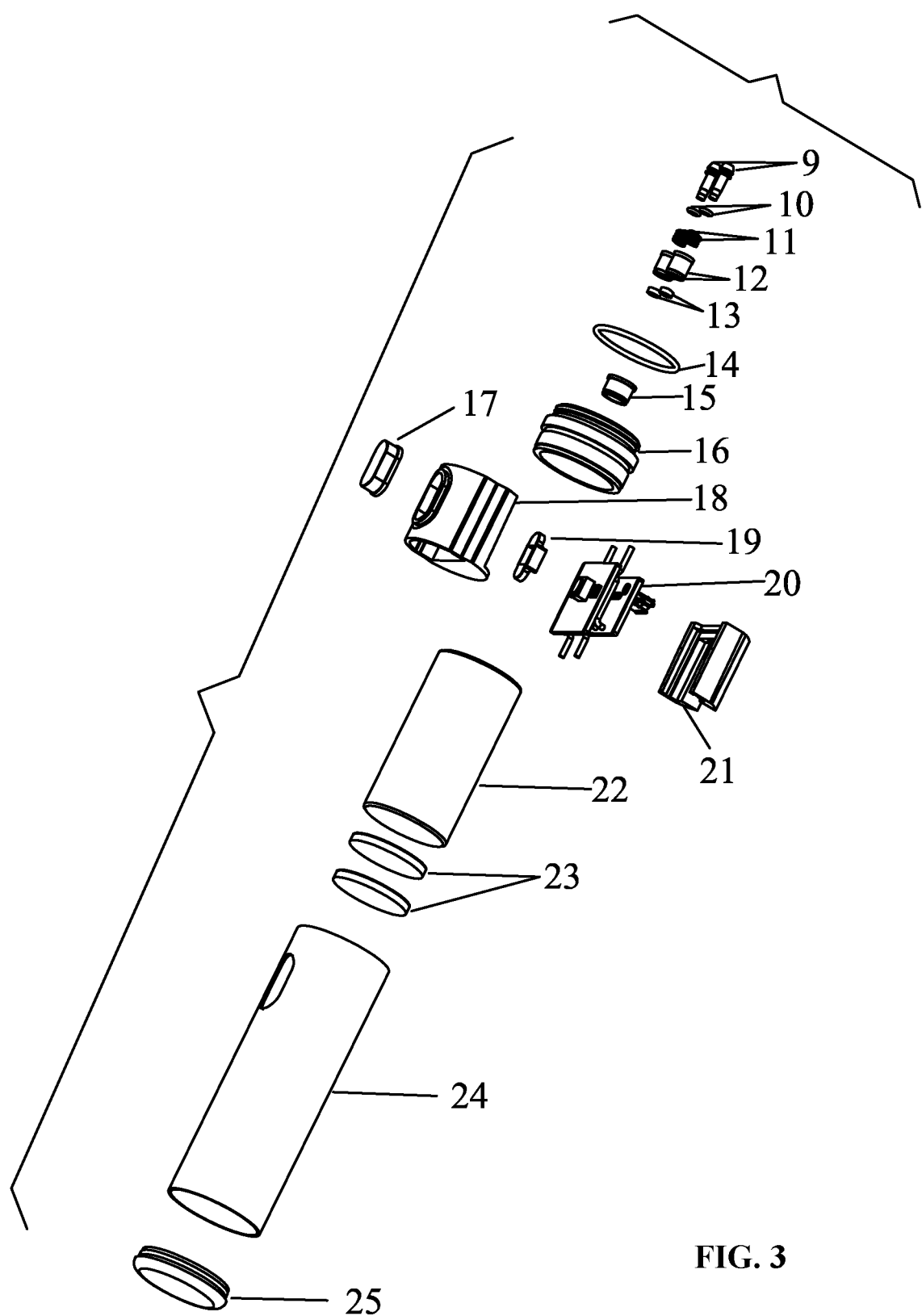
FIG. 3 is an exploded view of a battery assembly of an electronic cigarette as described in the disclosure.
Figure 4:
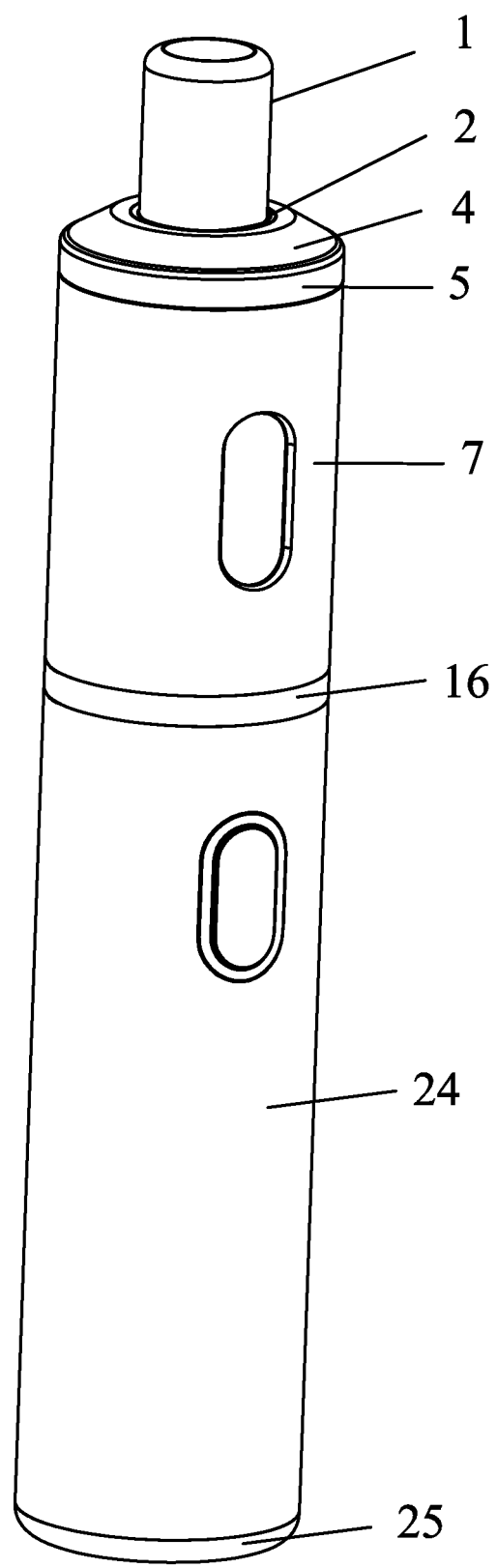
FIG. 4 is a stereogram of an electronic cigarette as described in the disclosure.
Figure 5:
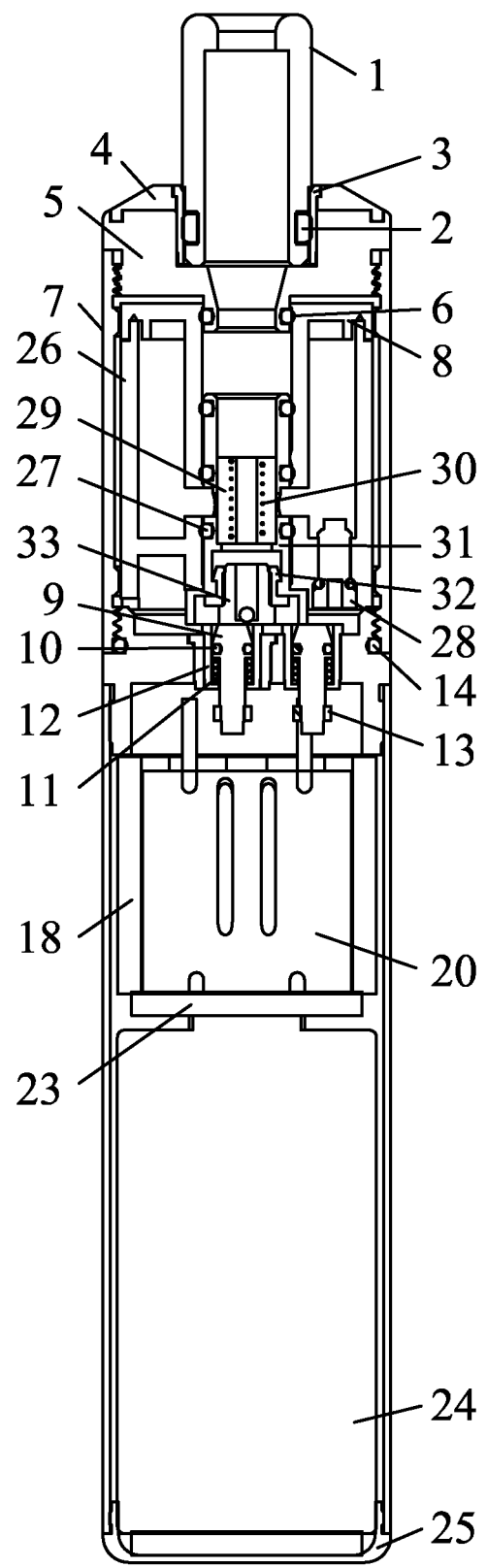
FIG. 5 is a sectional view of an electronic cigarette as described in the disclosure.

As shown in FIGS. 1-5, provided is an electronic cigarette comprising an atomization assembly A and a battery assembly B. The atomization assembly A is disposed on the battery assembly B. The atomization core is disposed in the atomization assembly.

The atomization assembly A comprises a mouthpiece 1, a first sealing ring 2 sealing the mouthpiece 1, an insulating gasket 4, a first fixing ring 3 fixing the insulating gasket 4, a mouthpiece holder 5, a second sealing ring 6 sealing the mouthpiece holder 5, an observation tube 7, a cover 8, an e-liquid chamber 26, O-rings 27, a seal plug 28, a piece of cotton 29, a heating wire 30, a limit cover 31, an insulation ring 32, and a joint 33.

The mouthpiece holder 5 comprises a groove and the second sealing ring 6 is embedded in the groove; the insulating gasket 4 is disposed on the mouthpiece holder 5; the first fixing ring 3 is sheathed on the insulating gasket 4; the first sealing ring 2 is sheathed on the mouthpiece 1; the mouthpiece 1 is in threaded connection to the first fixing ring 3. The cover 8 is disposed on the e-liquid chamber 26; the cotton 29 is sheathed on the heating wire 30; the heating wire 30 is disposed in the limit cover 31; the insulation ring 32 is disposed in the limit cover to separate positive and negative pins of the heating wire 30; the insulation ring 32 is sheathed on the joint 33; the O-rings 27 are sheathed on the limit cover 31; the O-rings 27, the seal plug 28, the cotton 29, the heating wire 30, the limit cover 31, the insulation ring 32, and the joint 33 form an atomization core; the atomization core is disposed in the e-liquid chamber 26; the seal plug 28 is disposed on one end of the chamber 26 away from the cover 8; the chamber 26 is in threaded connection to the mouthpiece holder 5; and the chamber 26 and the mouthpiece holder 5 are disposed in the observation tube 7.

The battery assembly comprises an electrode pole 9, a third sealing ring 10 sealing the electrode pole 9, an electrode output 11, a threaded sealing ring 12, a second fixing ring 13, a threaded ring 16, a fourth sealing ring 14 sealing the threaded ring 16, a nylon insulation ring 15, a press button 17, a control plate 20, a support 18, a silica pad 19, an observation window 21, a battery core 22, ring washers 23, a cartridge 24, and a battery cover 25.

The third sealing ring 10, the electrode output 11, the threaded sealing ring 12, and the second fixing ring 13 are sheathed on the electrode pole 9 in that order; the electrode pole 9 is disposed in the threaded ring 16; the nylon insulation ring 15 is sheathed on the electrode pole 9; the fourth sealing ring 14 is sheathed on the threaded ring 16; the silica pad 19 is disposed on the control plate 20; the control plate 20 is disposed on the support 18; the observation window 21 is fixed on the control plate 20; the press button 17 is disposed on the support 18; the support is disposed in the cartridge 24; and the ring washers 23 are disposed on two ends of the battery core 22, respectively; the ring washers 23 and the battery core 22 are disposed in the cartridge 24; the battery cover 25 is embedded in a first end of the cartridge 24 away from the mouthpiece; the threaded ring 16 is in threaded connection to a second end of the cartridge 24 opposite to the first end.

When the atomization assembly is not combined with the battery assembly, the e-liquid inlet of the limit cover 31 is separated from the chamber 26. No e-liquid enters the atomization core. When the atomization assembly is combined with the battery assembly, the electrode pole 9 pushes the atomization core to move towards the chamber 26, so that the e-liquid inlet of the limit cover 31 enters the chamber 26, and the e-liquid permeates into the atomization core. The observation tube comprises female threads, and the threaded ring comprises male threads matching the female threads. The atomization assembly is connected to the battery assembly via the female threads and the male threads. The electronic cigarette is cylindrical. The mouthpiece holder is in threaded connection to the chamber. When the atomization core requires renewal, loosen the threads to detach the mouthpiece holder from the chamber, and then the atomization core can be renewed.

It will be obvious to those skilled in the art that changes and modifications may be made, and therefore, the aim in the appended claims is to cover all such changes and modifications.

What is claimed is:

1. An electronic cigarette, comprising:
    an atomization assembly, the atomization assembly comprising a mouthpiece, a first sealing ring sealing the mouthpiece, an insulating gasket, a first fixing ring fixing the insulating gasket, a mouthpiece holder, a second sealing ring sealing the mouthpiece holder, an observation tube, a cover, an e-liquid chamber, O-rings, a seal plug, a piece of cotton, a heating wire, a limit cover, an insulation ring, and a joint; and
    a battery assembly, the battery assembly comprising an electrode pole, a third sealing ring sealing the electrode pole, an electrode output, a threaded sealing ring, a second fixing ring, a threaded ring, a fourth sealing ring sealing the threaded ring, a nylon insulation ring, a press button, a control plate, a support, a silica pad, an observation window, a battery core, ring washers, a cartridge, and a battery cover;
wherein:
    the atomization assembly is disposed on the battery assembly;
    the mouthpiece holder comprises a groove and the second sealing ring is embedded in the groove; the insulating gasket is disposed on the mouthpiece holder; the first fixing ring is sheathed on the insulating gasket; the first sealing ring is sheathed on the mouthpiece; the mouthpiece is in threaded connection to the first fixing ring;
    the cover is disposed on the e-liquid chamber; the cotton is sheathed on the heating wire; the heating wire is disposed in the limit cover; the insulation ring is disposed in the limit cover to separate positive and negative pins of the heating wire; the insulation ring is sheathed on the joint; the O-rings are sheathed on the limit cover; the O-rings, the seal plug, the cotton, the heating wire, the limit cover, the insulation ring, and the joint form an atomization core; the atomization core is disposed in the e-liquid chamber; the seal plug is disposed on one end of the chamber away from the cover; the chamber is in threaded connection to the mouthpiece holder; and the chamber and the mouthpiece holder are disposed in the observation tube;
    the third sealing ring, the electrode output, the threaded sealing ring, and the second fixing ring are sheathed on the electrode pole in that order; the electrode pole is disposed in the threaded ring; the nylon insulation ring is sheathed on the electrode pole; the fourth sealing ring is sheathed on the threaded ring; the silica pad is disposed on the control plate; the control plate is disposed on the support; the observation window is fixed on the control plate; the press button is disposed on the support; the support is disposed in the cartridge; and
    the ring washers are disposed on two ends of the battery core, respectively; the ring washers and the battery core are disposed in the cartridge; the battery cover is embedded in a first end of the cartridge away from the mouthpiece; the threaded ring is in threaded connection to a second end of the cartridge opposite to the first end.

2. The electronic cigarette of claim 1, wherein the observation tube comprises female threads, and the threaded ring comprises male threads matching the female threads.

* * * * *